United States Patent [19]

Dutta et al.

[11] Patent Number: 5,172,191
[45] Date of Patent: Dec. 15, 1992

[54] SWEEPING PHOTOREFLECTANCE SPECTROSCOPY

[75] Inventors: Mitra Dutta, Matawan; Hongen Shen, Howell, both of N.J.

[73] Assignee: The United States of America as represented by the Secretary of the Army, Washington, D.C.

[21] Appl. No.: 741,024

[22] Filed: Aug. 6, 1991

[51] Int. Cl.⁵ .................. G01N 21/55; G01N 21/84
[52] U.S. Cl. ......................... 356/432; 356/44
[58] Field of Search ............... 356/432 T, 445, 447, 356/448

[56] References Cited

U.S. PATENT DOCUMENTS

| | | | |
|---|---|---|---|
| 4,952,063 | 8/1990 | Opsal et al. | 356/432 |
| 4,953,983 | 9/1990 | Bottka et al. | 356/445 |
| 5,074,669 | 12/1991 | Opsal | 356/445 |

OTHER PUBLICATIONS

"New Normalization Procedure for Modulation Spectroscopy" by H. Shen, P. Parayanthal, Y. F. Liu, and Fred H. Pollak, Rev. Sci. Instrumentation, p. 1429-1432, Aug. 1987.

"Sweeping photoreflectance spectroscopy of semiconductors" by H. Shen and M. Dutta, Appl. Phys. Lett 57, pp. 587-589, Aug. 6, 1990.

Primary Examiner—Richard A. Rosenberger
Attorney, Agent, or Firm—Michael Zelenka

[57] ABSTRACT

A sweeping photoreflectance spectroscopy technique and apparatus is disclosed. This technique and apparatus enable the determination of the band structure of semi conductors and other materials at low temperatures by the mechanism of modulating the photoreflectance signal in a predetermined manner thereby enabling its detection in the presence of a much larger, but continuous, undesirable photoluminescence signal.

6 Claims, 1 Drawing Sheet

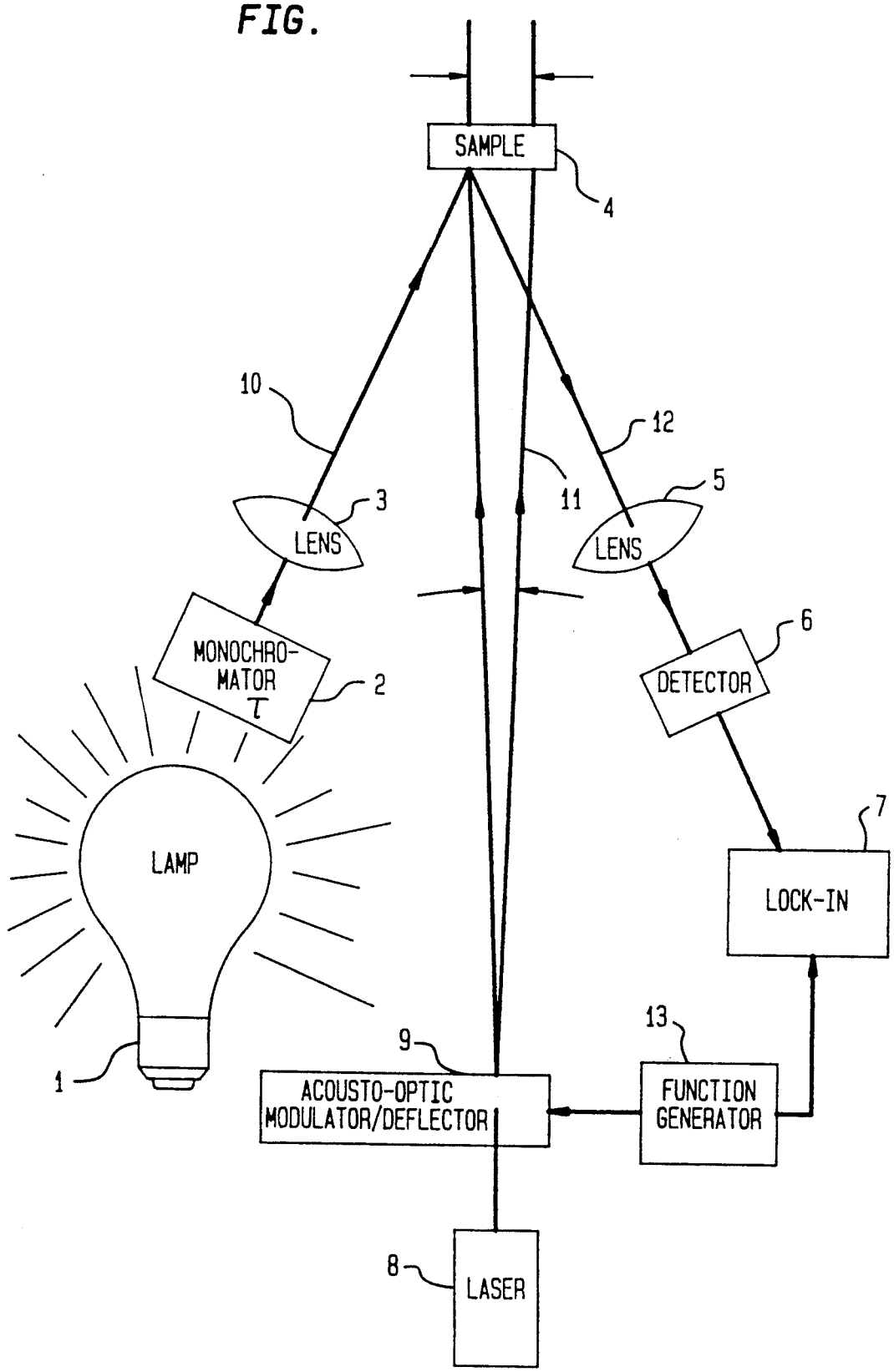

SWEEPING PHOTOREFLECTANCE SPECTROSCOPY

GOVERNMENT INTEREST

The invention described herein may be manufactured, used, and licensed by or for the Government for governmental purposes without the payment to me of any royalty thereon.

FIELD OF THE INVENTION

This invention relates in general to photoreflectance spectroscopy and more particularly a new method and apparatus therefore which teaches the technique of sweeping photoreflectance, which technique significantly reduces the effect of photoluminescence on photoreflectance measurements.

BACKGROUND OF THE INVENTION

Modulation spectroscopy has become a very important experimental tool to study semiconductors (bulk or thin film), semiconductor structures (superlattices, quantum wells, heterojunctions), and semiconductor interfaces (Schottky barriers, metal-insulator-semiconductor, semiconductor-electrolyte, etc.). Modulation spectra in semiconductors range in amplitude from $10^{-6}$ to as much as $10^{-2}$ and are, therefore, relatively easy to measure with modern analog phase-sensitive detection as used in lock-in amplifiers for example, or digital data processing techniques. The derivative nature of modulation spectra suppresses uninteresting background effects and emphasizes structure localized in the energy region of interband transitions. In addition, weak features that may not have been seen in absolute spectra are greatly enhanced.

One of the most commonly used of the modulation spectroscopy techniques is that of measuring photoreflectance. The advantage of this technique lies in its contactless, nondestructive character and experimental simplicity. In fact it is a favored room-temperature optical technique for semiconductor microstructure characterization. Modulation spectroscopy measuring photoreflectance has typically been accomplished by utilizing a pump beam for the purpose of electromodulation of the sample. The main illumination (probe) beam is swept over the frequency range of interest while illuminating the sample for which measurement is desired. At the same time, electromodulation of the sample is produced by the photoexcitation of electron-hole pairs by the pump beam, which is typically modulated by a chopper circuit. The reflected beam is then focused onto a detector and the photoreflectance of the sample under excitation is measured. A detailed description of this prior art technique may be found in the article entitled "New Normalization Procedure for Modulation Spectroscopy" authored by H. Shen, P. Parayanthal, Y. F. Liu and Fred H. Pollak, appearing at page 1429 of the Review of Science Instrumentation, August 1987. This article is hereby made a part hereof.

Recently photoreflectance measurements have been performed at elevated temperature up to 690° C. on GaAs, InP, AlGaAs, InGaAs, and AlGaAs/GaAs quantum wells. In spite of its success at high temperatures, there are only a few photoreflectance studies below 77 K. This is in part due to the fact that semiconductor samples (especially quantum wells and superlattices) tend to luminesce very efficiently. At low temperatures, the photoluminescence background is so strong that it masks the photoreflectance spectra. Two approaches have been used to solve this problem. One involves the use of a dye laser as a probe beam, and the other involves the use of a second synchronous monochromator before the detector as a band-pass filter.

The dye laser approach utilizes a laser that may be varied over a frequency range to generate the probe beam. This laser produces a more highly collimated beam of light than that produced by a lamp light channeled through a monochromator. Because this more highly collimated beam may be successfully detected if the detector is moved farther away from the sample the effect of the photoluminescence of the sample on the detector is reduced. The dye laser approach has the disadvantage of being more expensive than a lamp and monochromator system and of being more limited in frequency range than that system.

The use of a second synchronous monochromator for use as a bandpass filter before the detector stage will work, however some photoluminescence effect would still be present which would skew the reading. Further, synchronization of the monochromators has proven to be difficult.

The effects of these disadvantages and others are reduced or eliminated by the employment of applicants' invention as will be further described below.

BRIEF DESCRIPTION OF THE INVENTION

This invention entails the use of a sweeping photoreflectance apparatus and technique to overcome the problem of high photoluminescence levels masking the photoreflectance of a sample. In sweeping photoreflectance the mechanical chopper is replaced by an optical deflector. The pump beam is swept over a small area around the position of the probe beam on the samples. The sweeping of the pump beam is adjusted such that during a half period it is in coincidence with the probe beam, modulating the reflectance from the sample. During the other half period it sweeps away from the probe beam by a small distance and the reflected beam remains unperturbed. However, the pump beam still illuminates the sample thereby not diminishing its photoluminescence. The reflected beam is focused on a detector the output of which is coupled to a lock-in amplifier. The output of that lock-in device reveals the photoreflectance of interest.

This technique produces four signals. The first is a constant photoreflectance produced by the probe beam. The second is a constant photoluminescence signal caused by the probe beam and the pump beam as explained above. The third signal is a varying photoreflectance signal caused by the pump beam and probe beam alternately simultaneously illuminating and not simultaneously illuminating the same portion of the sample. Finally, the fourth signal is a small varying photoluminescence signal caused by the nonuniformity of the sample and/or the nonuniformity of the sensitivity of the detector active area. This fourth signal is very small with respect to the third signal and may be effectively ignored. The first and second signals being constant in nature, are filtered out and the photoreflectance information obtained from the third signal with minimal photoluminescence interference from the fourth signal. Hence the problem of photoluminescence signals masking the photoreflectance signal is eliminated.

BRIEF DESCRIPTION OF THE DRAWINGS

FIG. 1 is a block diagram representation of an apparatus suitable for practicing the invention.

DETAILED DESCRIPTION OF THE INVENTION

FIG. 1 is a block diagram representation of an apparatus suitable for practicing the invention. A similar figure appears in our article published in the Aug. 6, 1990 issue of Applied Physics Letters beginning at page 587. That article is hereby incorporated in this application by reference. Light from lamp 1 is directed through monochromator 2. The function of monochromator 2 is to provide a monochromatic light input to the lens 3. Lens 3 focuses this monochromatic light into probe beam 10 and onto the sample 4. During a portion of the time that sample 4 is illuminated by probe beam 10 that same portion of the sample is illuminated by pump beam 11. Pump beam 11 is generated by laser 8 and deflected by optical deflector 9 so as to repeatedly sweep onto and off of that portion of the sample 4 illuminated by the probe beam 10 but will not sweep off the sample in general. The output beam 12 is comprised of both a varying and constant photoreflectance signal, where the varying component is riding over the constant level. In addition, two photoluminescence signals are also present. They are generated by the material and radiate in all directions. One is a constant signal and the other a varying signal fluctuating at the frequency of the pump beam's coincidence with the probe beam. The constant photoluminescence signal is the combination of a signal caused by the constant exposure of the sample 4 to the probe beam 10 and the constant exposure of the sample 4 to the pump beam 11. The varying photoluminescence signal is a result of nonuniformity of the sample 4 and/or nonuniformity of the sensitivity of the detector 6. Both the photoreflectance and photoluminescence signals are focused through lens 5 onto the detector 6. The output of detector 6 is electrically coupled to lock-in amplifier 7 A second input to lock-in amplifier 7 is provided by an electrical signal from function generator 13. The input into function generator 13 is a signal from optical deflector 9. Function generator 13 has the characteristic of matching the optical deflection of the optic deflector 9 with an internally generated electrical waveform. That electrical waveform is then electrically coupled to lock-in amplifier 7 and serves as a reference signal for that device to establish the varying signal of interest, that is, the varying component of the photoreflectance signal. The varying component of the photoluminescence signal is very small and has essentially no effect on the photoreflectance signal of interest.

All components of this invention are known devices in the art and may be commercially obtained. For example, the following is a representative list of some of the equipment which might be used.

| 1. Function Generator | Model No. 72-380 TENMAC Test Instruments Corporation 650 Congress Park Dr. Centerville, Ohio 45459-4072 |
|---|---|
| 2. Lock-in Amplifier | Model No. 5210 EG & G Princeton Applied Research Co. P.O. Box 2565 Princeton, N.J. 08543 |
| 3. Acoustio-Optic Modulator/Deflector | Model No. N21080-1SAS Newport Electro-Optics |

-continued

| | System Inc. 4451-B Enterprise Ct. Melbourne, Florida 32935 |
|---|---|

It is to be understood that we do not desire to limit this invention to the exact configuration or technique described for obvious modifications still contemplated by our invention will occur to a person skilled in the art.

What is claimed is:

1. A sweeping photoreflectance method for measuring the photoreflectance of a sample of material, which material has the characteristic of its photoluminescence signal masking its photoreflectance signal, by:
    illuminating an area of the sample of interest with a first beam of light for some time period of illumination, t1;
    illuminating the sample with a second beam of light which second beam, while at all times of interest illuminating the sample, is, for some portion of the period of illumination t1, directed so as to further illuminate said first area of the sample already illuminated by said first beam of light for some period of time, and, for some second period of time, directed so as to illuminate a second portion of the sample chosen for some portion of the time period of illumination, t1, in some known illumination sequence, so that the total photoluminescence signal from the sample is essentially constant during the period of both illuminations;
    detecting the light reflected and emitted from the sample of interest; and
    filtering the component of the reflected beam consistent with the known illumination sequence of the area of sample of interest so as to examine that component of the reflected beam resulting from the photoreflectance of the sample when exposed to the first and second beam of light.

2. The method of claim 1 wherein the first beam of light is varied in frequency.

3. The method of claim 2 wherein the known illumination sequence is periodic.

4. Apparatus for measuring the photoreflectance of a sample of material, which material has the characteristic of its photoluminescence signal masking its photoreflectance signal comprising:
    a first light source means for projecting a first focused beam of monochromatic light over a frequency range of interest onto an area of a sample;
    a second light source means for projecting a second monochromatic beam of light continuously onto the sample in general in the vicinity of, but not on, that portion of the sample illuminated by the first light source means, and, at predetermined times, onto that portion of the sample illuminated by said first beam of light;
    means for collecting the light reflected from and generated by the sample containing information as to the structure of the sample; and
    means for extracting that information relative to the photoreflectance of the sample from the light collected.

5. The apparatus of claim 4 wherein the first light source means comprises a lamp, a monochromator through which the light from the lamp passes and a focusing lens which focuses the first focused beam.

6. The apparatus of claim 5 wherein said second light source comprises a laser and an optical deflector and wherein the light from said laser is directed by the optical deflector.

* * * * *